United States Patent [19]

Robson et al.

[11] 4,221,673

[45] Sep. 9, 1980

[54] METAL PHENATES

[75] Inventors: Robert Robson, Oxford, England; Brian Swinney, Ontario, Canada; Robert D. Tack, Oxford, England

[73] Assignee: Exxon Research & Engineering Co., Florham Park, N.J.

[21] Appl. No.: 871,016

[22] Filed: Jan. 20, 1978

[30] Foreign Application Priority Data

Jan. 28, 1977 [GB] United Kingdom ............... 3556/77

[51] Int. Cl.$^2$ ................. C10M 1/54; C10M 1/42; C10M 1/20; C10M 3/48
[52] U.S. Cl. ............................. 252/42.7; 252/389 R; 568/763; 568/796; 568/23; 568/40
[58] Field of Search .................... 252/42.7, 389 R; 260/608, 609 F; 568/763, 796

[56] References Cited

U.S. PATENT DOCUMENTS

| | | | |
|---|---|---|---|
| 2,061,111 | 11/1936 | Stevens et al. | 23/239 |
| 2,062,676 | 12/1936 | Reiff | 87/9 |
| 2,116,220 | 5/1938 | Shoemaker | 87/19 |
| 2,194,312 | 3/1940 | Loane | 87/9 |
| 2,253,228 | 8/1941 | Cantrell et al. | 252/46 |
| 2,280,419 | 4/1942 | Wilson | 252/33 |
| 2,315,072 | 3/1943 | Nelson et al. | 252/48 |
| 2,388,887 | 11/1945 | Weissberger et al. | 252/316 |
| 2,426,549 | 8/1947 | Coppock | 252/52 |
| 2,429,905 | 10/1947 | Wright | 252/52 |
| 2,512,784 | 6/1950 | Adelson | 252/48.2 |
| 2,623,855 | 12/1952 | Garner | 252/48.2 |
| 2,680,097 | 6/1954 | Stewart | 252/42.7 |
| 3,043,672 | 7/1962 | Ecke et al. | 44/69 |
| 3,725,381 | 4/1973 | Sakai et al. | 252/42.7 |
| 3,755,170 | 8/1973 | Rogers et al. | 252/42.7 |

*Primary Examiner*—Delbert E. Gantz
*Assistant Examiner*—Irving Vaughn
*Attorney, Agent, or Firm*—Frank T. Johmann

[57] ABSTRACT

Metal phenates especially overbased phenates are prepared by reacting a basic metallic compound with a mixture of an alkyl phenol and an alkyldihydroxybenzene. The products are useful as lubricant additives with improved antirust properties, and when overbased, with higher basicity and lower viscosity.

18 Claims, No Drawings

METAL PHENATES

The present invention relates to improved metal phenates and particularly to calcium phenates, especially overbased calcium phenates, which are useful as lubricant additives.

Neutral and overbased metal phenates are well-known as is their use as lubricant additives. The term overbased is used to describe compounds containing more than the stoichiometric amount of metal required to react with the phenol. Metal phenates are based on alkali or alkaline earth metals the most common being calcium, barium and magnesium and may be based on normal phenols or sulphurised phenols as is appropriate.

There is extensive patent literature on the production of neutral and overbased metal phenates especially on calcium and magnesium phenates. For example U.S. Pat. Nos. 3,718,589; 3,746,698 and 3,755,170, British Pat. No. 1,469,289 and Belgian Pat. No. 842,131 all describe the production of overbased additives especially overbased magnesium additives. British Pat. No. 1,470,338 describes another process which is particularly suited to obtain overbased calcium additives.

Overbased phenates, especially sulphurised phenates have detergent properties and are widely used as dispersants in lubricants. The overbased materials are particularly useful since their high basicity neutralises acids formed in the lubricant. Although calcium additives are cheaper than the corresponding magnesium additives, one advantage of using magnesium additives is that in addition to their dispersant and neutralising properties they also impart antirust properties to the lubricant which is not the situation with calcium additives. In addition the magnesium additives have a higher base number per weight of metal which is desirable since the less metal present in an oil the smaller the amounts of deposit formed during use of the oil.

There is therefore a considerable incentive to develop calcium phenates with improved antirust properties or to develop magnesium phenates which are more potent antirust additives so as to allow less of them to be used to achieve the desired antirust properties. We have found that this may be achieved if the phenolic component used in the preparation of the metal phenate consists in part of a derivative of catechol or resorcinol, especially a catechol derivative.

The present invention therefore provides a process for the production of metal phenates comprising reacting an alkali or alkaline earth metal base with a phenolic composition, said phenolic composition comprising:

(i) from 50% to 90% by weight of an alkyl phenol of the general formula:

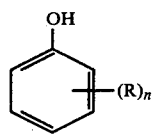

where n is from 1 to 5 and R is a hydrocarbyl or substituted hydrocarbyl group containing up to 60 carbon atoms and from 50% to 10% by weight of a dihydroxy benzene of the general formula

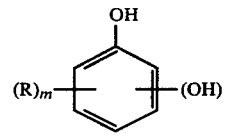

where m is from 1 to 4, R is as defined above and the hydroxyl groups are either ortho or meta to each other;

(ii) the composition described under (i) above admixed with sulphur; or (iii) from 50% to 90% by weight of a sulphurised alkyl phenol of the general formula:

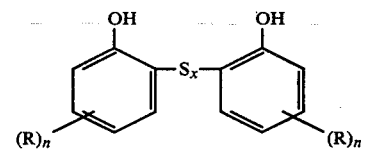

where R is as defined above, n is 1 to 4 and x is from 1 to 4 and from 50% to 10% by weight of a sulphurised dihydroxy benzene of the general formula:

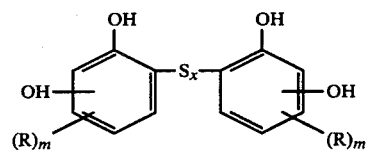

where R and x are as defined above, m is 1 to 3 and the hydroxyl groups are either ortho or meta to each other; or (iv) any mixture of two or more of (i), (ii) and (iii) above.

The sulphurised phenols and dihydroxybenzenes are generally mixtures of compounds having different values of x so reference to the value of x quoted herein is the average value. Where the products of the invention are to be used as lubricant addivites we prefer that at least one of the alkyl groups on the aromatic nucleus of both the phenol and the dihydroxybenzene contain at least seven carbon atoms. In particular we prefer that at least one alkyl group contain from 9 to 15 carbon atoms since compounds without an alkyl group containing as many as 9 carbon atoms have limited oil solubility. Typically, then in our preferred composition, both the phenol and the dihydroxybenzene carry a nonyl, decyl, dodecyl or tetradecyl substituent. The alkyl substituents on the phenol and the didhydroxybenzene may be the same or different. Although the alkyldihydroxybenzene may be based on catechol or resorcinol, we prefer that it be an alkyl catechol.

Where the process of the present invention involves reacting the alkyl phenol, the alkyldihydroxy benzene, the metal base and sulphur, the sulphur will surphurise the phenol and the dihydroxybenzene, yielding:

(i) sulphurised phenol,
(ii) sulphurised dihydroxybenezene, and
(iii) mixed sulphurised phenol dihydroxybenzenes of the formula:

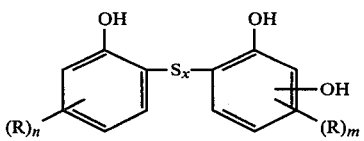

so the product of the reaction of the present invention will be derived from a mixture of the three materials described above.

The techniques of the present invention may be used to produce metal phenates of any suitable alkali or alkaline earth metal. For example the metal may be sodium, potassium or lithium, or as is preferred, an alkaline earth metal such as magnesium or barium or, as is more preferred calcium. The invention is particularly useful in the production of overbased calcium phenates where the presence of the dihydroxybenzene imparts antirust activity, in some instances producing a material having equal potent antirust properties to the more expensive overbased magnesium phenates and sulphurised phenates derived from alkyl phenols. It also appears that the presence of the dihydroxybenzene may enable higher base number calcium phenates having acceptable viscosities to be produced.

The reaction between the alkali or alkaline earth metal and the phenolic composition may be carried out in any of the well known methods. For example the metal may be mixed with the phenolic composition in the form of its alkoxide and the mixture then hydrolysed to liberate the metal hydroxide as is described in Belgian Pat. No. 842,131. The metal hydroxide will then react with the phenolic composition to form the metal phenate and where excess metal ions above the stoichiometric amount required to neutralise the phenolic composition have been added to produce an overbased material, the excess may be neutralised by blowing with carbon dioxide to convert the metal to its carbonate which will be suspended by the surfactant effect of the metal phenate. Alternatively the metal alkoxide may be carbonated prior to reaction with the phenolic composition as is described in U.S. Pat. Nos. 3,150,088 and 3,150,089. These techniques are particularly suited when the metal is magnesium.

Alternatively the metal oxide or hydroxide may be reacted with the phenolic composition. Where these techniques are used to produce overbased magnesium additives, a highly active form of magnesium oxide of high surface area is preferably used together with a carboxylic acid or ester promoter such as is described in British Pat. No. 1,469,289. And where magnesium additives are being produced, we prefer to use an already sulphurised phenolic composition rather than a mixture of sulphur and the phenolic composition. If however this technique is used to produce calcium additives, either an already sulphurised phenolic composition or a mixture of the phenolic composition and sulphur may be used.

The techniques of our invention may therefore be applied to any of the processes used to make neutral and overbased phenates. Generally these reactions are carried out in an oil solution and a second solvent may be used if necessary, and reaction promoters may also be used.

The techniques of our invention may be used in any of the previously suggested processes for the production of overbased phenates from alkaline earth metals employing any suitable reaction promoter system, most of which require the presence of low molecular weight alcohols or glycols, often in association with other promoters such as higher alcohols, carboxylic acids or nitrogen containing organic compounds.

The relative quanitites of the reactants that should be used will depend upon the product required. For example in the production of neutral metal phenates the metal ions should be substantially stoichiometrically equivalent to the phenate ions present. If overbased additives are to be produced, an excess of metal ions should be used to yield free metal ions suspended in the metal phenate detergent and, if desired, these may be neutralised by an acid gas such as carbon dioxide to yield a colloidal metal salt (carbonate when the gas is carbon dioxide) suspended in the metal phenate.

The relative proportions of the alkyl phenol and alkyldihydroxybenzene that should be used depend upon the nature of the metal ion and the desired properties of the product. Economically it is preferable to use as little alkyldihydroxy benzene as possible since they are considerably more expensive than most phenols. In the production of calcium phenates for lubricant additives we have found that at least 10 wt.% of the alkyl dihydroxybenzene based on the total weight of the phenolic composition should be included to achieve a significant increase in the antirust properties, however if more than 50% by weight of the phenolic composition is the alkydihydroxybenzene the overbased calcium sulphurised phenates have an unacceptably high viscosity. We therefore prefer to use phenolic compositions containing from 10% to 50% by weight of the alkyldihydroxybenzene. We also find in the production of overbased materials that if the alkyl dihydroxybenzene is present as more than 35% by weight of the phenolic composition the oil solubility of the overbased phenate is reduced. Furthermore there is a tendency for the overbased phenate to have an undesirably dark colour. Thus, in the preparation of overbased phenates we prefer to use a phenolic composition containing from 15% to 35% by weight of the alkyldihydroxybenzene, especially in the production of overbased calcium sulphurised phenates.

In addition in the production of our preferred overbased calcium sulphurised additives we prefer that the phenolic composition contain the phenol and the dihydroxybenzene and sulphur, rather than the sulphurised materials, since the product tends to have improved oil solubility. Our preferred process for the production of overbased calcium sulphurised additives is described in British Pat. No. 1,470,338 which is included herein by reference. Our preferred processes for the production of overbased magnesium sulphurised additives are described in British Pat. No. 1,469,289 and Belgian Pat. No. 842,131 which are also included herein by reference.

According to a further embodiment of our invention, we add a minor amount of a sulphonate or a sulphonic acid to the reaction mixture. We find that in some instances the presence of the sulphonic acid or sulphonate gives the final product improved solubility in highly viscous oils and also reduces the tendency of the product to form a skin. We believe that the presence of the sulphonate or sulphonic acid helps to stabilise the colloid and we find that best results are obtained if it is added to the initial reaction mixture prior to carbonation and that up to about 6% by weight of sulphonate or sulphonic acid based on the weight of final product is sufficient to achieve the desired effect. The preferred sulphonic acids are the oil soluble alkylaryl sulphonic acids and the preferred sulphonates are the salts of these acids. Particularly preferred are the sulphonates or sulphonic acids derived from alkyl benzenes or alkyl xylenes.

Our preferred overbased product is found to be a colloidal suspension in oil of Group IIA metal basic compounds, mainly carbonate but including basic carbonate, oxide or hydroxide together with Group IIA metal surfactants as dispersant with the average diameter of the colloidal particles generally being less than 60 Å. Usually the finished product is 50–70% e.g. 60% active ingredients in oil. Its TBN (Total Base Number) can vary from 150 to 400, usually 200–300, e.g. 240–260.

The major constituents of the preferred Group IIA metal sulphurised phenates obtained by our process have the structure:

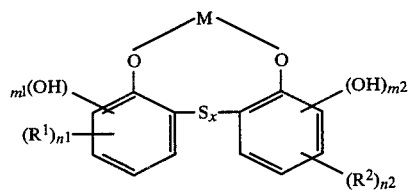

where M is the Group IIA metal, $R^1$ and $R^2$ are hydrocarbyl groups, $n^1$ and $n^2$ are one or more and may be the same or different, and $m^1$ and $m^2$ are 1 or zero and may be the same or different with at least one of $m^1$ and $m^2$ being 1, and when $m^1$ and/or $m^2$ is 1 the hydroxyl is in the ortho or meta position with respect to the phenoxy radical linked to the metal atom M. The final product is generally a mixture of such phenates where x, $n^1$, $n^2$, $m^1$ and $m^2$ vary for different molecules. Minor amounts of compounds in which more than two aromatic rings are joined by sulphur links may be present. However generally n is 1 and/or 2 and x is 1 or 2 and possibly 3 or 4, with an average value of from 1.5 to 2.

Overbased metal phenates prepared by the process of this invention are very suitable as detergent additives for lubricating oils where their detergent properties inhibit formation of undesirable sediments whilst their high Total Base Number (TNB), due to the excess metal present, neutralises acids which may originate from fuel combustion thus reducing engine corrosion. The presence of the dihydroxybenzene has been found to give improved antirust properties. The lubricating oils with which the products are used can be any animal, vegetable or any of the traditional mineral oils, for example petroleum oil to SAE 30, 40 or 50 lubricating oil grades, castor oil, fish oils or oxidised mineral oil.

Alternatively the lubricating oil can be a synthetic ester lubricating oil and these include diesters such as dioctyl adipate, dioctyl sebacate, didecyl azelate, tridecyl adipate, didecyl succinate, didecyl glutarate and mixtures thereof. Alternatively the synthetic ester can be a polyester such as that prepared by reacting polyhydric alcohols such as trimethylolpropane and pentaerythritol with monocarboxylic acids such as butyric acid to give the corresponding tri- and tetra- esters. Also complex esters may be used, such as those formed by esterification reactions between a carboxylic acid, a glycol and an alcohol or a monocarboxylic acid.

The overbased detergent is generally added to the lubricating oil as a concentrate and we find that between 0.01% and 30% by weight, preferably between 0.1% and 5% by weight of a concentrate consisting of 60 wt.% metal carbonate plus metal sulphurised phenate and 40 wt.% oil is particularly useful.

The final lubricating oil composition may if desired contain other additives e.g. a Viscosity Index improver such as an ethylenepropylene copolymer, an overbased calcium sulphonate or a dispersant such as polyisobutylene succinamide.

The present invention is illustrated but in no way limited by reference to the following examples.

EXAMPLE 1

The following materials were charged to a reaction vessel:

| | | |
|---|---|---|
| 864 grams | dodecyl phenol | } Phenolic composition |
| 216 grams | nonyl catechol | |
| 540 grams | ethylene glycol | |
| 360 grams | tridecanol | |
| 252 grams | flowers of sulphur | |
| 379 grams | calcium oxide | |
| 728 grams | non-volatile diluent oil | | and heated to 110° C. and carbon dioxide passed through the mixture while it was being stirred. The temperature was then allowed to rise to 180° C. over a period of two hours and held at that temperature for 10 hours until the mixture was neutral to phenolphthalein.

The mixture was then heated to 210° C. under 100 millimeter mercury pressure to distil off the glycol and tridecanol. And after filtration 2,605 grams of a product having a total base number equivalent to 253 milligrams of KOH per gram and a kinematic viscosity of 210° F. of 448 centistokes were obtained.

EXAMPLE 2

The process of Example 1 was repeated with varying proportions of dodecyl phenol and nonyl catechol in the phenolic composition. In all instances 1080 grams of the phenolic composition were used. The TBN, viscosities and sulphur contents of the products obtained are set out in the following table:

| Phenolic Composition Wt. % of Component based on Composition Wt. | | | | |
|---|---|---|---|---|
| Nonyl Catechol | Dodecyl Phenol | TBN (mg KOH/gram) | Product Kinematic Viscosity cS | Sulphur Wt. % |
| 0 | 40 | 240 | 300 | 3.0 |
| 8 | 32 | 266 | 510 | 3.4 |
| 8 | 32 | 257 | 591 | 3.2 |
| 12 | 28 | 341 | | 3.83 |
| 20 | 20 | 277 | 2289 | 3.04 |
| 28 | 12 | 296 | | 3.05 |
| 40 | 0 | Solidified on Addition of Calcium Oxide | | |

EXAMPLE 3

A neutral calcium phenate was prepared by charging:

| | |
|---|---|
| 319 grams | dodecyl phenol |
| 80 grams | nonyl catechol |
| 180.5 grams | ethylene glycol |
| 44 grams | flowers of sulphur |

| | |
|---|---|
| 47 grams | calcium oxide | to a reaction vessel heated to 150° C. and the temperature raised to 180° C. over one hour to remove hydrogen sulphide. The product was then heated at 210° C. and 100 millimeters mercury pressure to remove the glycol. Finally 141 grams of non-volatile diluent oil were added and the product filtered to yield 461.5 grams of a mineral having a base number of 144 milligrams of KOH per gram and a viscosity of 425 centistokes at 210° F.

EXAMPLE 4

The product of Example 1 was included in a lubricating oil based on a MIL-C formulation and containing 3.7 wt.% of an ashless polyamine dispersant, 1.2 wt.% of a neutral calcium phenate, 1.2 wt.% of a zinc dialkyldithiophosphate and 1.2 wt.% of magnesium sulphonate.

The performance of this oil was compared with a similar oil in which the product of Example 1 was replaced by a material in which the nonyl catechol was replaced by more dodecyl phenol. Both oils were subject to the MSIIC antirust test (ASTM STP 315F) and that containing the product of Example 1 had a test result of 8.1 whilst the result for the other was 7.1.

EXAMPLE 5

126 grams of dodecyl phenol, 54 grams of nonyl catechol, 90 grams of ethylene glycol and 60 grams of tridecanol were charged to a 1 liter flask through which nitrogen was bubbled at 100 ml/minute and the flask heated at 50° C. 42 grams of flowers of sulphur were then added over a 10 minute period and 63 grams of calcium oxide added during the following 10 minutes.

An exothermic reaction took place and when the temperature reached 110° C., 70 grams of a non-volatile paraffinic diluent oil were added. The nitrogen supply was then replaced by a stream of carbon dioxide at 120 ml/minute and the temperature increased to 150° C. over a period of 1 hour.

The temperature was then further increased to 180° C. to distil off the water/ethylene glycol azeotrope. Carbonation was continued for a further 6 hours after which the carbon dioxide stream was replaced by nitrogen and the product stripped at 210° C. and 100 millimeters mercury pressure for 2 hours. Finally the material was filtered and washed twice with 20 grams of the diluent oil.

345 grams of filtrate were obtained containing 10.73 wt.% calcium and 3.25 wt.% sulphur. The viscosity was 1984 centistokes at 210° F. with a TBN of 290 milligrams KOH per gram.

Samples of the product were diluted with further diluent oil to determine the viscosity at certain TBN's with the following results:

| TBN milligrams KOH/gram | Viscosity Centistokes at 210° F. |
|---|---|
| 264.7 | 623.9 |
| 251.9 | 324.8 |
| 224.6 | 116.17 |

EXAMPLE 6

154 grams of nonyl phenol sulphide containing 7.7 wt.% sulphur, 17 grams of nonyl catechol sulphide containing 8.3 wt.% sulphur, an oil solution containing 13 grams of a 90 wt.% active ingredient solution of an alkylated benzene sulphonic acid of molecular weight 490, 256 grams of magnesium 2-ethoxy ethoxide and 135 grams of oil were charged to a flask and heated at 60° for 15 minutes. 32.4 grams of water and 32.4 g of 2-ethoxyethanol were added and $CO_2$ passed through the mixture for 5 hours. The mixture was stripped at 150° C./100 mm Hg. 14 grams of oil were added, to give after filtration a product, with a total base number of 247 mg KOH/g., containing 5.5 wt.% magnesium and 3.54 wt.% sulphur. The viscosity of 210° F. was 417 centistokes.

EXAMPLE 7

137 grams of nonyl phenyl sulphide containing 7.7 wt.% sulphur, 34 grams of nonyl catechol sulphide containing 8.3 wt.% sulphur, 13 grams of an oil solution of a 90 wt.% active solution of an alkylated benzene sulphonic acid of molecular weight 490, 256 grams of magnesium 2-ethoxy ethoxide and 133 grams of oil were charged to a flask and heated at 60° for 15 minutes. 32.4 grams of water and 32.4 grams of 2-ethoxy ethanol were added and $CO_2$ passed through the mixture for 6 hours. 14 grams of oil was added and the mixture stripped at 150° C./100 mm. to give after filtration a product, with a total base number of 240 mg KOH/g, containing 5.3 wt.% magnesium and 3.66 wt.% sulphur. The viscosity at 210° F. was 1022 centistokes.

EXAMPLE 8

240 grams of nonyl phenol sulphide containing 7.7 wt.% sulphur, 60 grams of nonyl catechol sulphide contaning 8.3 wt.% sulphur, 75 grams of methanol, 150 grams of toluene and 40 grams of oil were heated to 50° C. and 20.4 grams of magnesium oxide added. After refluxing for two hours the mixture was stripped at 150° C./100 mm and 14 grams of oil added to give after filtration a product, with a total base number of 114 mg.KOH/g, containing 2.5 wt.% magnesium and 5.97 wt.% sulphur. The viscosity at 210° F. was 220 centistokes.

EXAMPLE 9

80 grams of dodecyl phenol sulphide containing 7.1 wt.% sulphur, 20 grams of nonyl catechol sulphide containing 8.3 wt.% sulphur 117 grams of toluene and 100 grams of methanol were heated to 60° C. Then 30 grams of calcium oxide and 2 grams of ethanolamine were added and $CO_2$ bubbled through the solution for 2 hours. The solution was stripped at 150° C./60 mm and 64 grams of oil added to give after filtration a product, with a total base number of 220 mgKOH/g, containing 6.6 wt.% calcium and 2.9 wt.% sulphur. The viscosity at 210° F. was 362 centistokes.

EXAMPLE 10

171 grams of dodecyl phenol sulphide containing 7.0 wt.% sulphur, 43 grams of nonyl catechol sulphide contaning 8.3 wt.% sulphur, 72 grams of ethylene glycol and 53 grams of isodecanol were heated to 50° C. and 20 grams of calcium oxide added. The mixture was heated to 180° C. and then cooled to 160° C. when a further 32 grams of calcium oxide were added. Carbon dioxide was bubbled through the mixture, which was heated to 180° C. for 5 hours. The mixture was stripped to 210° C./60 mm and 58 grams of oil added to give after filtration a product, with a total base number of 227 mg KOH/g, containing 7.8 wt.% calcium and 3.0 wt.% sulphur.

EXAMPLE 11

80 grams of dodecyl phenol sulphide containing 7.5 wt.% sulphur, 20 grams of nonyl catechol sulphide containing 8.3 wt.% sulphur, 100 grams of toluene and 50 grams of methanol were heated to 50° C. and 16.8 grams calcium oxide added. The mixture was refluxed for two hours, stripped to 150° C./60 mm and 20 grams of oil added to give after filtration a product, with a total base number of 122 mg KOH/g, containing 4.0 wt.% calcium and 4.7 wt.% sulphur. The viscosity of 210° F. was 1282 centistokes.

EXAMPLE 12

283.5 grams of dodecyl phenyl, 31 grams of nonyl catechol, 33 grams of ethylene glycol and 4.5 grams of calcium oxide were stripped at room temperature for an hour. The pressure was then reduced to 15 mm and the mixture heated to 130° C. for 1½ hours. 37 grams of oil were then added and the mixture stripped at 150°/15 mm to give after filtration a product with a total base number of 13 mg KOH/g and containing 0.45 wt.% Calcium.

We claim:

1. A process for the production of sulfurized and non-sulfurized metal phenates useful as lubricant additives comprising reacting an alkali or alkaline earth metal base with a phenolic composition, said phenolic composition comprising:

(i) from 50% to 90% by weight of an alkyl phenol of the general formula:

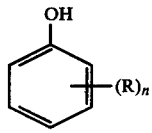

where n is from 1 to 5 and R is an alkyl group containing up to 60 carbon atoms, and from 50% to 10% by weight of an alkyl dihydroxy benzene of the general formula:

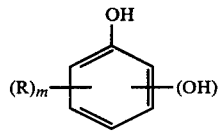

where m is from 1 to 4, R is as defined above and the hydroxyl groups are either ortho or meta to each other; or (ii) the composition described under (i) above admixed with sulphur; or (iii) from 50% to 90% by weight of a sulphurised alkyl phenol of the general formula:

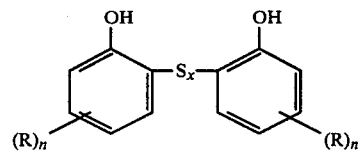

where R is as defined above, n is 1 to 4 and x is from 1 to 4, and from 50% to 10% by weight of a sulphurised alkyl dihydroxy benzene of the general formula:

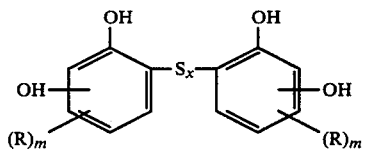

where R, and x are as defined above, m is 1 to 3 and the hydroxyl groups are either ortho or meta to each other; or (iv) any mixture of two or more of (i), (ii) and (iii) above, and wherein at least one of the alkyl groups on the aromatic nucleus of both the phenol and the dihydroxy benzene contains at least 7 carbon atoms.

2. A process according to claim 1 in which the alkyl group contains from 9 to 15 carbon atoms.

3. A process according to claim 1 in which the metal base is an alkaline earth metal base.

4. A process according to claim 3 in which the alkaline earth metal base is magnesium base.

5. A process according to claim 3 in which the alkaline earth metal base is calcium base.

6. A process according to claim 3 in which said alkaline earth metal base is an alkoxide.

7. A process according to claim 3 in which said alkaline earth metal base is an oxide.

8. A process according to claim 1 in which said phenolic composition comprises said mixture of 50 to 90% by weight of alkyl phenol and from 10 wt. % to 50 wt. % of said alkyldihydroxybenzene based on the total weight of said phenolic composition.

9. A process according to claim 1 in which a stoichiometric excess of said metal base is used above that required to react with said phenolic composition.

10. A process according to claim 9 in which the excess of said metal base is converted to its carbonate by carbonating the reaction mixture.

11. A sulphurised metal phenate composition useful as a lubricant additive which is a mixture comprising constituents of the general formula:

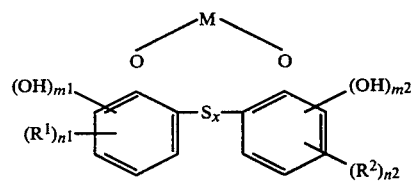

wherein M is a Group IIA metal, $R^1$ and $R^2$ are alkyl groups, $n^1$ and $n^2$ are one or more and may be the same or different, and $m^1$ and $m^2$ are 1 or zero and may be the same or different, at least one of $m^1$ and $m^2$ being 1 and when $m^1$ and/or $m^2$ is 1 the hydroxyl is in the ortho or meta position with respect to the phenoxy radical linked to the metal atom M and x is from 1 to 4, said composition being the reaction product of Group IIA metal base with a phenolic composition selected from the group consisting of: (i) a mixture of 50 to 90 wt. % of alkyl phenol and 50 to 10% alkyl dihydroxy benzene with sulfur, and (ii) 50 to 90 wt. % of sulfurized alkyl phenol and 50 to 10 wt. % of sulfurized alkyl dihydroxy benzene; and wherein at least one of the alkyl groups on the aromatic nucleus of both the phenol and the dihydroxy benzene contains at least 7 carbon atoms.

12. A sulphurised metal phenate composition according to claim 11 in which M is calcium.

13. A sulphurised metal phenate composition according to claim 11 in which M is magnesium.

14. A lubricating composition comprising a major amount of an oil and a minor amount of sulphurised metal phenate composition according to claim 11.

15. A sulfurized metal phenate composition according to claim 11, wherein said composition is overbased by use of a stoichiometric excess of said metal base above that required to react with said phenolic composition.

16. A sulfurized metal phenate composition according to claim 15, wherein said excess metal base is converted to its carbonate by carbonating the reaction mixture.

17. A sulfurized metal phenate composition according to claim 11, wherein said alkyl groups contain 9 to 15 carbon atoms.

18. A sulfurized metal phenate composition according to claim 11, wherein said alkyl phenol is dodecyl phenol and said alkyl dihydroxy benzene is nonyl catechol.

* * * * *